(12) United States Patent
Serban et al.

(10) Patent No.: US 8,544,314 B2
(45) Date of Patent: *Oct. 1, 2013

(54) CARBON DIOXIDE SENSOR WITH FUNCTIONALIZED RESONATING BEAMS

(75) Inventors: Bogdan Catalin Serban, Bucharest (RO); Cornel P. Cobianu, Bucharest (RO); Mihai N. Mihaila, Bucharest (RO); Viorel Georgel Dumitru, Prahova (RO)

(73) Assignee: Honeywell Romania S.R.L., Bucharest (RO)

( * ) Notice: Subject to any disclaimer, the term of this patent is extended or adjusted under 35 U.S.C. 154(b) by 414 days.

This patent is subject to a terminal disclaimer.

(21) Appl. No.: 12/962,170

(22) Filed: Dec. 7, 2010

(65) Prior Publication Data

US 2011/0138878 A1 Jun. 16, 2011

(30) Foreign Application Priority Data

Dec. 11, 2009 (EP) .................................. 09178787

(51) Int. Cl.
*G01N 30/96* (2006.01)
*G01N 29/036* (2006.01)
(52) U.S. Cl.
USPC .......................................... 73/24.01; 422/88
(58) Field of Classification Search
USPC ...................... 73/23.3, 24.01; 422/83, 84, 88
See application file for complete search history.

(56) References Cited

U.S. PATENT DOCUMENTS

| 3,879,992 | A  | * | 4/1975  | Bartera ........................ 73/24.01 |
| 5,719,324 | A  | * | 2/1998  | Thundat et al. .............. 73/24.01 |
| 7,584,649 | B2 | * | 9/2009  | Shaw et al. .................. 73/31.06 |
| 7,914,740 | B2 | * | 3/2011  | Zhang et al. ................. 422/68.1 |
| 8,230,720 | B2 | * | 7/2012  | Serban et al. ................ 73/24.01 |
| 2004/0016287 | A1 | * | 1/2004  | Fu ................................ 73/23.34 |
| 2005/0003560 | A1 | * | 1/2005  | Zeng et al. .................... 436/527 |
| 2006/0223171 | A1 | * | 10/2006 | Craighead et al. .......... 435/287.2 |
| 2008/0054382 | A1 | * | 3/2008  | Stetter .......................... 257/414 |
| 2008/0110247 | A1 |   | 5/2008  | Shaw et al. |
| 2010/0000292 | A1 | * | 1/2010  | Karabacak et al. .......... 73/24.01 |
| 2010/0137731 | A1 | * | 6/2010  | Star et al. ..................... 600/532 |
| 2011/0113856 | A1 | * | 5/2011  | Cobianu et al. .............. 73/24.06 |
| 2011/0116974 | A1 |   | 5/2011  | Serban et al. |

(Continued)

FOREIGN PATENT DOCUMENTS

EP 0072744 A2 2/1983
WO WO 2005026694 A2 * 3/2005

OTHER PUBLICATIONS

Serban, Bogdan, Cornel Cobianu, and Cazimir Bostan. "Novel Concepts for CO2 Detection by Differential Resonant Nanosensing." Nano-Electro-Mechanical Devices for Integrated Sensing and Switching Satellite workshop to ESSDERC/ESSCIRC, 2010.*

(Continued)

*Primary Examiner* — Lisa Caputo
*Assistant Examiner* — Punam Roy
(74) *Attorney, Agent, or Firm* — Schwegman, Lundberg & Woessner, P.A.

(57) ABSTRACT

A carbon dioxide sensor comprising a first beam that includes a functionalized surface and a second beam that includes a functionalized surface such that reduced-drift differential sensing of carbon dioxide may be performed by monitoring changes in the resonant frequency of the first beam relative to the resonant frequency of second beam.

15 Claims, 6 Drawing Sheets

(56) References Cited

U.S. PATENT DOCUMENTS

| | | | |
|---|---|---|---|
| 2011/0138878 A1* | 6/2011 | Serban et al. | 73/24.02 |
| 2011/0143447 A1* | 6/2011 | Serban et al. | 436/117 |
| 2011/0143448 A1* | 6/2011 | Serban et al. | 436/122 |
| 2011/0239759 A1* | 10/2011 | Cobianu et al. | 73/335.03 |
| 2012/0142135 A1* | 6/2012 | Cobianu | 438/49 |
| 2012/0164029 A1* | 6/2012 | Serban et al. | 422/82.01 |

OTHER PUBLICATIONS

Serban, B.; Sarin Kumar, A.K.; Cobianu, C.; Buiu, O.; Costea, S.; Bostan, C.; Varachiu, N., "Selection of gas sensing materials using the Hard Soft Acid Base theory; application to Surface Acoustic Wave CO2 detection," Semiconductor Conference (CAS), 2010 International, pp. 247-250, Oct. 11-13, 2010.*

Cobianu, C.; Serban, B.; Georgescu, I.; Costea, Stefan; Bostan, C., "A novel concept for low drift chemical sensing at micro and nano-scale," Semiconductor Conference (CAS), 2010 International, pp. 217-220, Oct. 11-13, 2010.*

"European Application Serial No. 09178787.9, Office Action mailed Jun. 15, 2010", 6 pgs.

"European Application Serial No. 09178787.9, Office Action Response filed Oct. 15, 2010", 2 pgs.

"European Application Serial No. 09178787.9, Search Report mailed May 26, 2010", 4 Pgs.

Cobianu, C., et al., "Nano-scale resonant sensors for gas and bio detection: Expectations and challenges", International Semiconductor Conference, 2009. CAS 2009., XP031568982 ISBN : 978-1-4244-441,3-7, (2009), 259-262.

Durand, C, et al., "In-Plane Silicon-On-Nothing Nanometer-Scale Resonant Suspended Gate MOSFET for In-IC Integration Perspectives", IEEE Electron Device Letters, 29(5), XP0L1207042 ISSN: 0741-3106, (2008), 494-496.

* cited by examiner

CARBON DIOXIDE SENSOR WITH FUNCTIONALIZED RESONATING BEAMS

RELATED MATTERS

This application claims priority under 35 USC §119 to European Application Serial Number 09178787.9, filed Dec. 11, 2009, which is incorporated herein by reference in its entirety.

BACKGROUND

The global efforts on preserving the health of the planet are focused in some key area like global warming and environmental air quality. One aspect of improving environmental air quality relates to technologies where the carbon dioxide that is released from manufacturing processes is captured and sequestered.

Capturing and sequestering carbon dioxide may in the near future involve tightly controlled processes that include continuous real-time monitoring of carbon dioxide emissions. The processes and monitoring that are typically associated with capturing and sequestering carbon dioxide often require high cost-high power carbon dioxide sensors.

One potential technology that may be utilized to produce low-cost and low-power carbon dioxide sensors involves integrated resonant sensing technology. This integrated sensing technology is based on vibrating beams that are functionalized for chemisorptive carbon dioxide capture. The beams are typically doubly clamp (nano)beams, cantilever (nano) beams or even nanowires. The beams change their resonance frequency proportional to the amount of $CO_2$ adsorbed on the beam.

These functionalized resonant sensing beams are typically located on the same chip with an integrated circuit for processing signals from the carbon dioxide sensor. A typical single silicon wafer having diameter of 400 mm may contain hundreds of thousands of on-chip carbon dioxide Nano-Electro-Mechano Sensors and Integrated Circuits (NEMSIC) that communicate with the readout integrated circuit.

One of the drawbacks with existing resonant NEMSIC gas sensing systems may relate to the baseline drift of the chemical sensor. The baseline drift is typically caused by the harmful effects of temperature variation, humidity and aging of the functionalized beams. These harmful effects often reduce the accuracy of the sensor response.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, electrical, and optical changes may be made without departing from the scope of the present invention. The following description of example embodiments is, therefore, not to be taken in a limited sense, and the scope of the present invention is defined by the appended claims.

Figure 1:
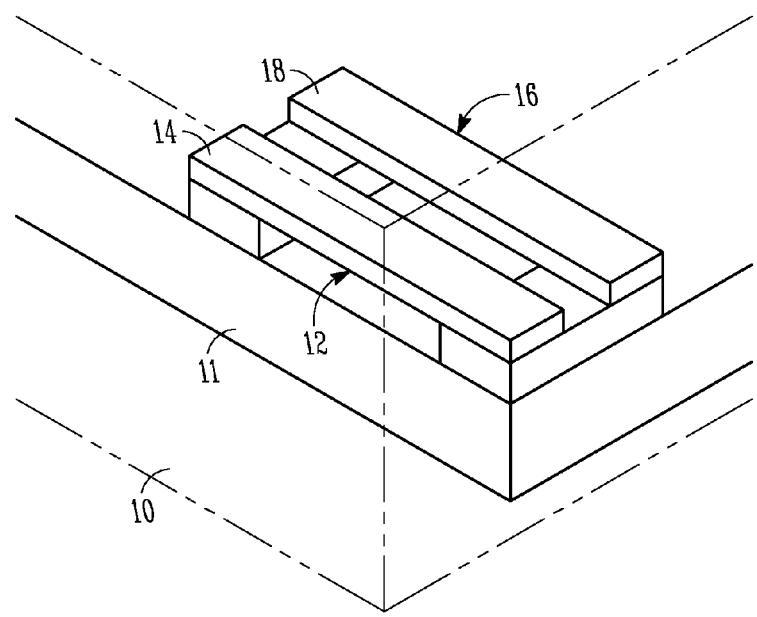
FIG. 1 illustrates a carbon dioxide sensor according to an example embodiment.

FIG. 1 illustrates an example carbon dioxide sensor 10. The carbon dioxide sensor 10 includes a substrate 11 with a first beam 12 and a second beam 16 formed on the substrate 11. Although the first and second beams 12, 16 are shown on the same substrate 11, embodiments are contemplated where the first and second beams 12, 16 are on different substrates.

Figure 2:
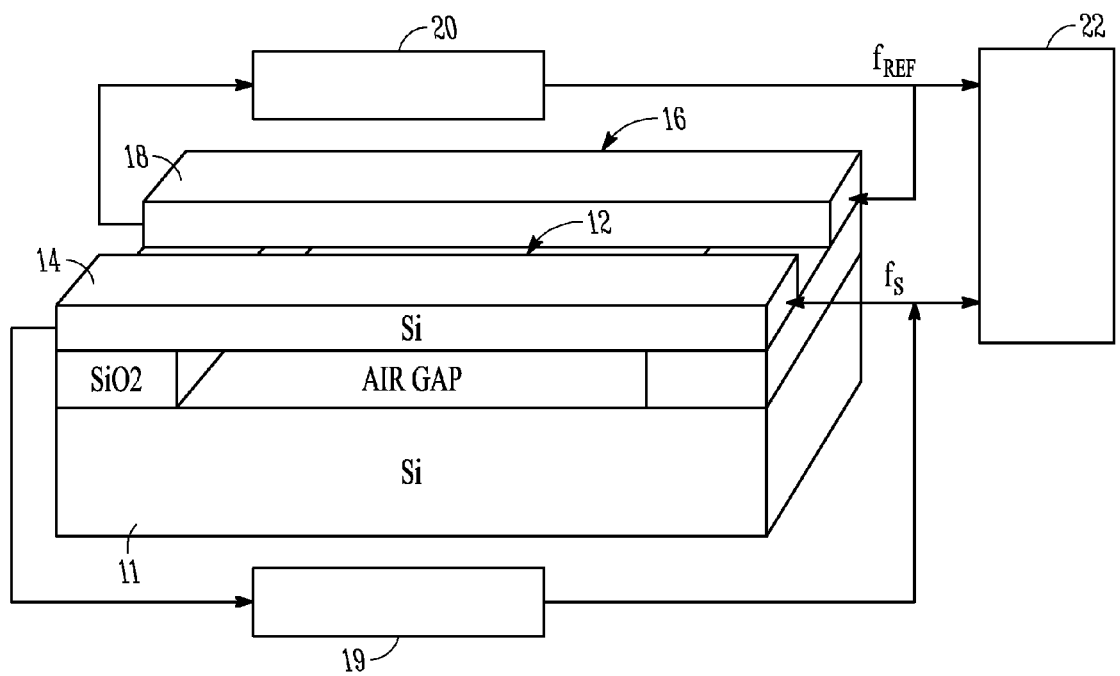
FIG. 2 is an enlarged view illustrating a portion of the carbon dioxide sensor shown in FIG. 1.

FIG. 2 is an enlarged view illustrating a portion of the carbon dioxide sensor shown in FIG. 1. The first beam 12 includes a functionalized sensing surface 14 and the second beam 16 includes a functionalized reference surface 18. The carbon dioxide sensor 10 performs differential sensing of carbon dioxide by monitoring changes in the resonant frequency of the first beam 12 relative to the resonant frequency of second beam 16.

As used herein, a "functionalized surface" means a surface that is capable of absorbing and/or reacting with carbon dioxide. It should be noted that the functionalized surfaces 14, 18 may be part of the first and second beams 12, 16 or formed as part of a layer or coating that is added to the first and second beams 12, 16. In addition, a functionalized surface may be altered by some method to inhibit adsorption of carbon dioxide. In the illustrated example embodiment, the functionalized surface 18 is altered by exposing the functionalized surface 18 to HCl to inhibit adsorption of carbon dioxide by the functionalized surface 18.

The carbon dioxide sensor 10 may further include a first frequency measuring electronic circuit 19 that measures the resonant frequency of the first beam 12 and a second frequency measuring electronic circuit 20 that measures the resonant frequency of the second beam 16. In some embodiments, each of the frequency measuring circuits 19, 20 includes an electronic circuit that has the respective vibrating (resonant) first and second beams 12, 16 within feed-back loops that are associated with each frequency measuring circuit 19, 20.

The vibrating first and second beams 12, 16 may include a small-signal electrical equivalent circuit that comprises a series circuit made of an electrical (motional) resistance, an electrical (motional) inductance and an electrical (motional) capacitance. The quantitative values of these electrical equivalent components are influenced by the mass which is loading each of the vibrating beams.

The resonance frequency of the each vibrating beam depends on the geometry, active mass and stiffness of each beam as well as the clamping mode to the substrate. The resonance frequency of the each vibrating beam depends the external pressure at which each beam exposed as well as any additional mass loading on the vibrating beams. In some of the embodiments described herein, the mass loading provides information about any accreted mass on the vibrating beam. The electrical circuit for frequency measurement tracks the resonance frequency of the vibrating beam based on the feed-back loop concept.

It should be noted that the first and second frequency measuring circuits 19, 20 may be a variety of electronic circuits. As an example, the first and second frequency measuring circuits 19, 20 may be a Phase Lock Loop (PLL) circuit where the frequency of each vibrating beam 12, 16 may be followed by a voltage control oscillator (VCO). The VCO may be driven by a quasi dc control signal, which is proportional with the frequency difference between the resonance frequency of the beam and frequency of the VCO. The feed-back loop of the PLL may act so that the operating frequency of the VCO becomes equal with the resonance frequency of the corresponding vibrating beam.

As another example, the frequency measurement circuit 19 and 20 may be similar to approaches that are used for MEMS-based electronic oscillators. Each vibrating beam may be located in the feedback loop of an oscillator such that the resonance frequency of the beam determines the resonance frequency of the oscillator.

An example differential sensing concept is shown in application Ser. No. 61/262,702 (filed on Nov. 19, 2009 and incorporated herein by reference) where the baseline drift of the sensor due to temperature, humidity, aging effects which can affect the resonance frequency of the first and second beams 12, 16 is eliminated. In the example embodiment illustrated in FIG. 2, the first and the second frequency measuring circuits 19, 20 send signals to a control 22. The frequency measuring circuit 19 sends signal to the control 22 with a frequency that equal to the resonance frequency of the first beam 12 and frequency measuring circuit 20 sends signal to the control 22 with a frequency that equal to the resonance frequency of the second beam 16.

In some embodiments, the control 22 may be an electronic mixer which receives the frequency signals the first and the second frequency measuring circuits 19, 20 and creates an output signal that has a frequency which is equal to the difference of the two frequencies. Thus, the contribution of the "common mode signals" like humidity, aging and temperature on the resonance frequency of each of the first and second beams 12, 16 can be reduced or eliminated by subtracting the resonance frequency of the first beam 12 and second beam 16. The frequency difference provided by the controller 22 provides information about the carbon dioxide gas that is detected by the carbon dioxide sensor 10.

In some embodiments, the functionalized sensing surface 14 of the first beam 12 and the functionalized sensing surface 18 of the second beam 16 contain carbon dioxide sensitive terminal groups such as 1,8 diaza bicyclo[5,4,0]undec-7-ene (DBU). In other embodiments, the functionalized surfaces 14, 18 contain carbon dioxide sensitive terminal groups such as diaza-bicyclo[4,3,0]-non-5-ene (DBN). DBU and DBN are strong basis that belong to the class of cyclic amidine, and at room temperature are reversible when reacting with carbon dioxide and water (which always exists in the ambient). This reaction (with either DBU or DBN) produces a bicarbonate salt resident on the functionalized sensing surface 14 of the first beam 12 which changes the resonant frequency of the first beam 12.

In some embodiments, the functionalized reference surface 18 of the second beam is similar to the DBN and DBU functionalized sensing surfaces 14 described above because the functionalized reference surface 18 may be formed on the substrate 11 in a manner similar to the functionalized sensing surface 14 described above. However, the amidine moieties of the functionalized reference surface 18 on the second beam 16 may be converted into hydrochlorides (e.g., by exposure to HCl) such that there is no sensitivity to carbon dioxide on the reference loop.

Using first and second beams 12, 16 that include the functionalized sensing surface 14 and functionalized reference surface 18 as described above makes them suitable for differential sensing because they have similar physical responses to temperature, humidity and aging. These similar physical responses allow "common mode signals" to be eliminated while differential signals (which contain only carbon dioxide responses) remain accurate and drift-free.

In some embodiments, the first and second beams 12, 16 may be made of silicon such that functionalization of the DBU or DBN may be done near the end of SOI-MEMS-CMOSFET wafer processing to partially (or wholly) form the functionalized sensing surface 14 and functionalized reference surface 18 (i.e., after the release of the suspended silicon first and second beams 12, 16 by silicon dioxide etching in a fluorine-based agent).

Figure 3:
FIG. 3 illustrates native oxide removal from a suspended silicon beam in 1% HF for getting an H-terminated silicon beam surface.
Figure 4:
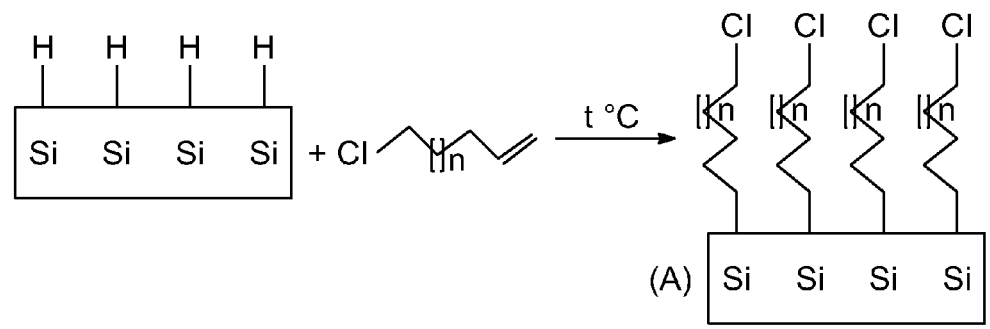
FIG. 4 illustrates the suspended silicon beam of FIG. 3 after immersion of the suspended silicon beam to get a layer of alkyl chloride connected to the silicon surface by carbon atoms.
Figure 5:
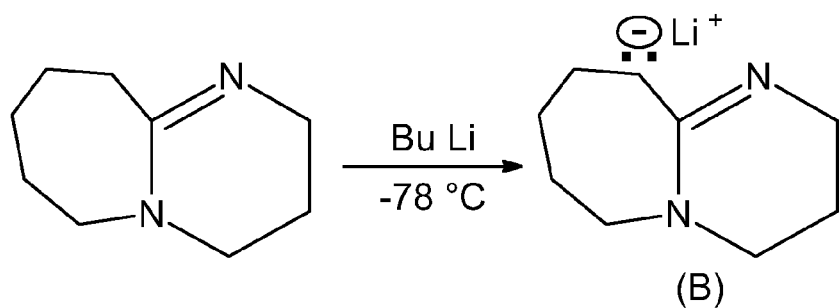
FIG. 5 illustrates the deprotonation of DBU at −78 Celsius degrees in the presence of butyl lithium.
Figure 6:
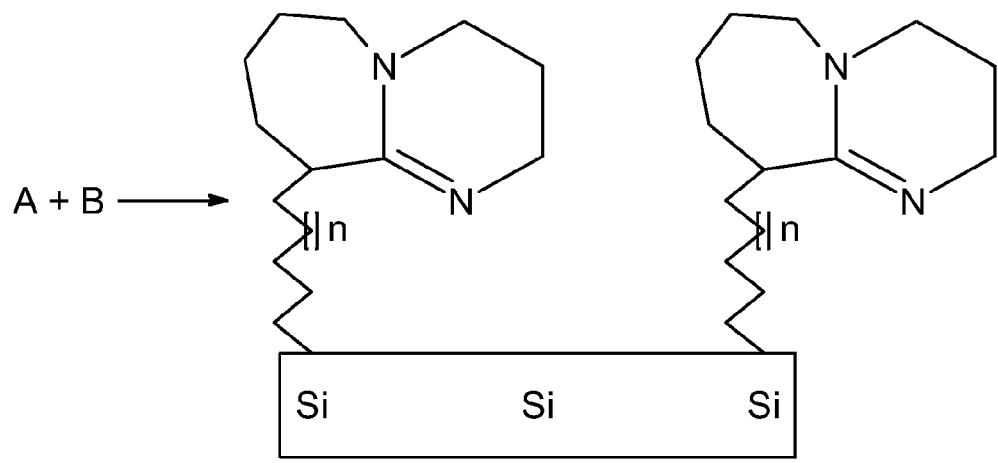
FIG. 6 illustrates the suspended silicon beam of FIG. 4 after reaction of deprotonated DBU with an alkyl chloride layer.

As an example, the DBU sensing moieties may be connected to the silicon surfaces of the suspended silicon first and second beams 12, 16 by means of alkyl chain groups. An example sequence of DBU of a functionalization process is described below:

1. Wafer cleaning avoiding sticking of the suspended beams to the substrate.
2. Native oxide removal from suspended Si beam in 1% HF for getting H-terminated silicon beam surface (see FIG. 3).
3. Immersion of the wafers containing suspended first and second beams having the hydrogen-terminated surface in a flask containing unsaturated alkyl halide such as alkyl chloride and toluene followed by heating the sealed flask at 150° C. for 4 hours for getting a monolayer of this alkyl chloride connected to the silicon surface by carbon atoms (see FIG. 4).
4. Rinsing the wafers in isopropyl alcohol followed by cleaning and drying to avoid suspended beams sticking to the substrate.
5. Deprotonation of the DBU at −78 Celsius degrees, in the presence of butyl lithium as shown in (see FIG. 5).
6. Reaction of deprotonated DBU with alkyl chloride monolayer from the silicon surface in order to obtain the $CO_2$ sensing layer based on the DBU moiety where the deprotonated group is connected to alkyl chloride removing the chlorine atoms (see FIG. 6).

Figure 7:
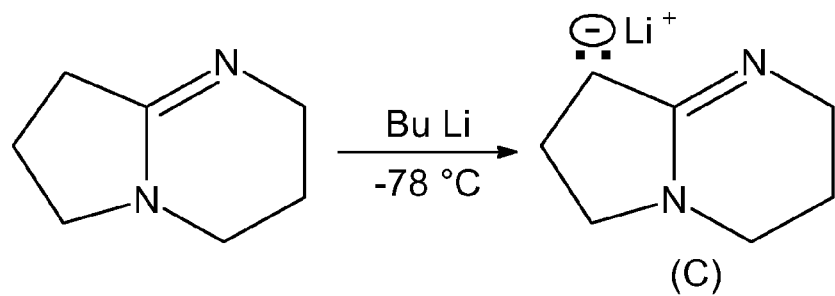
FIG. 7 illustrates the deprotonation of DBN at −78 Celsius degrees in the presence of butyl lithium.
Figure 8:
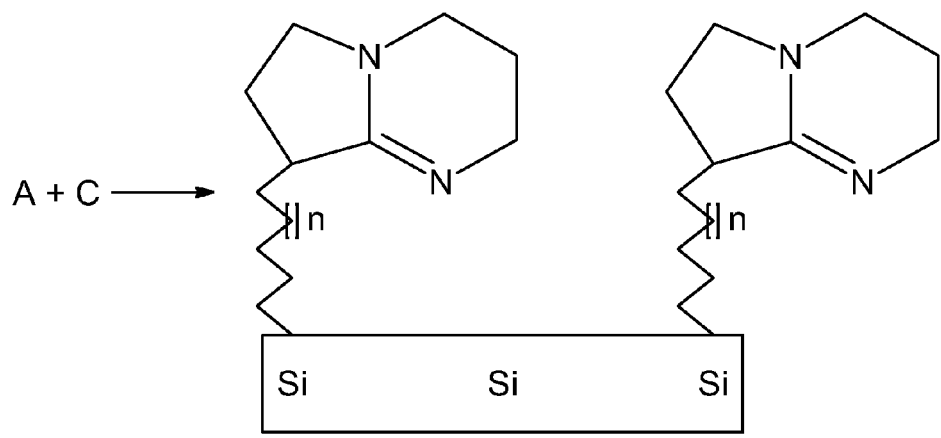
FIG. 8 illustrates the suspended silicon beam of FIG. 4 after reaction of deprotonated DBN with an alkyl chloride layer.

A similar approach is followed for the DBN functionalization process where depronated DBN (see FIG. 7) reacts with alkyl chloride layer from the silicon surface in order to obtain a beam surface with DBN moiety (see FIG. 8). This type of reaction makes the beams suitable sensing carbon dioxide.

Figure 9:
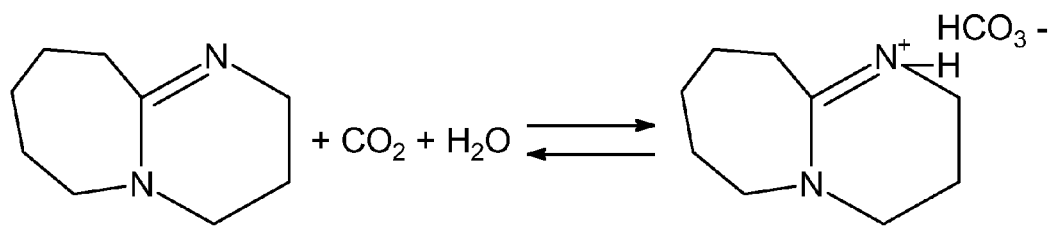
FIG. 9 shows the reversible reaction of DBU functionalized surface with carbon dioxide and water to form bicarbonate salt as a reaction product.
Figure 10:
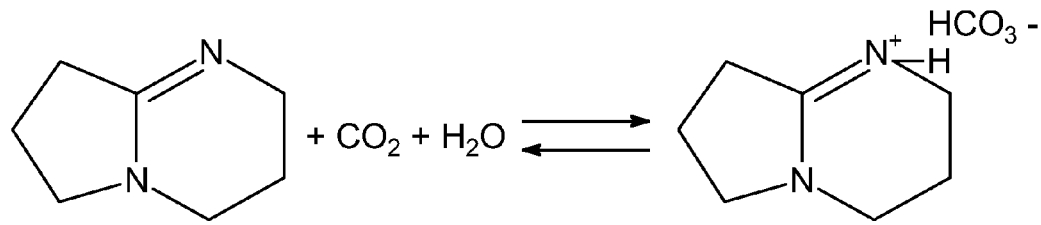
FIG. 10 shows the reversible reaction of DBN functionalized surface with carbon dioxide and water to form bicarbonate salt as a reaction product.

FIG. 9 shows the reversible reaction of DBU functionalized surface with carbon dioxide and water forming bicarbonate salt as a reaction product. FIG. 10 shows the reversible reaction of DBN functionalized silicon surface with carbon dioxide and water to give the same bicarbonate salt.

In some embodiments, the functionalized reference surface 18 on the second beam 16 may be made right along with the DBN (or DBU) based sensor the functionalized sensing surface 14 on the first beam 12. The functionalized reference surface 18 is made insensitive to carbon dioxide by subsequent reaction of the DBN (or DBU) based surface with HCl in order to inactivate the DBN (or DBU) moiety (e.g., by selective direct printing of liquid HCl on the site of the future second beam 16).

Figure 11:
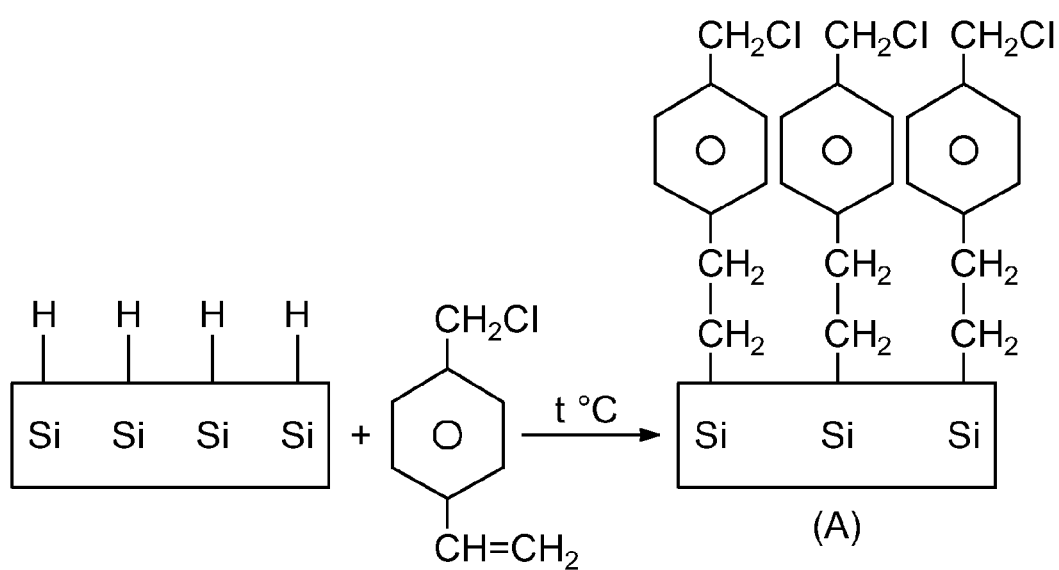
FIG. 11 illustrates the suspended silicon beam of FIG. 3 after immersion of the suspended silicon beam to get a layer of chloromethylated styrene connected to the silicon surface by styrene moiety.
Figure 12:
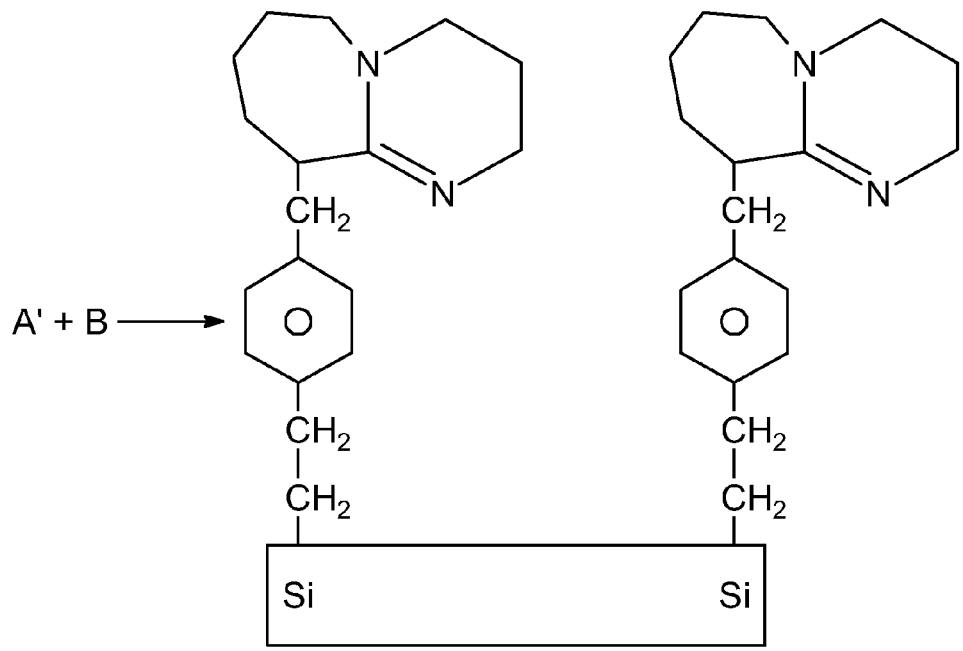
FIG. 12 illustrates the suspended silicon beam of FIG. 11 after reaction with deprotonated DBU to synthesize a functionalized surface connected by styrene moiety.

As another example, the DBU or DBN sensing moieties may be connected to the silicon surfaces of the suspended silicon first and second beams by means of styrene moiety. An example sequence of this type of DBU functionalization processing is described below:

1. Wafer cleaning to prevent sticking of the suspended first and second silicon beams 12, 16 to the substrate 11.
2. Native oxide removal from suspended first and second silicon beams 12, 16 in 1% HF for getting H-terminated silicon beam surface (see FIG. 3).
3. Immersion of the wafers containing suspended first and second silicon beams 12, 16 having hydrogen-terminated surfaces in flask containing chloromethylated styrene and toluene followed by heating the sealed flask at 150° C. for 4 hours for getting a layer of chloromethylated styrene connected to the Si surface by styrene moiety (see FIG. 11).
4. Rinsing wafers in isopropyl alcohol followed by cleaning and drying so as to prevent suspended first and second silicon beams 12, 16 from sticking to the substrate.
5. Deprotonation of the DBU at −78 Celsius degrees, in the presence of butyl lithium (see FIG. 5).
6. Reaction of deprotonated DBU (compound B from FIG. 5) with compound A' in order to synthesize the DBU based sensing surface which is connected by styrene moiety to the Si surface (see FIG. 12).

Figure 13:
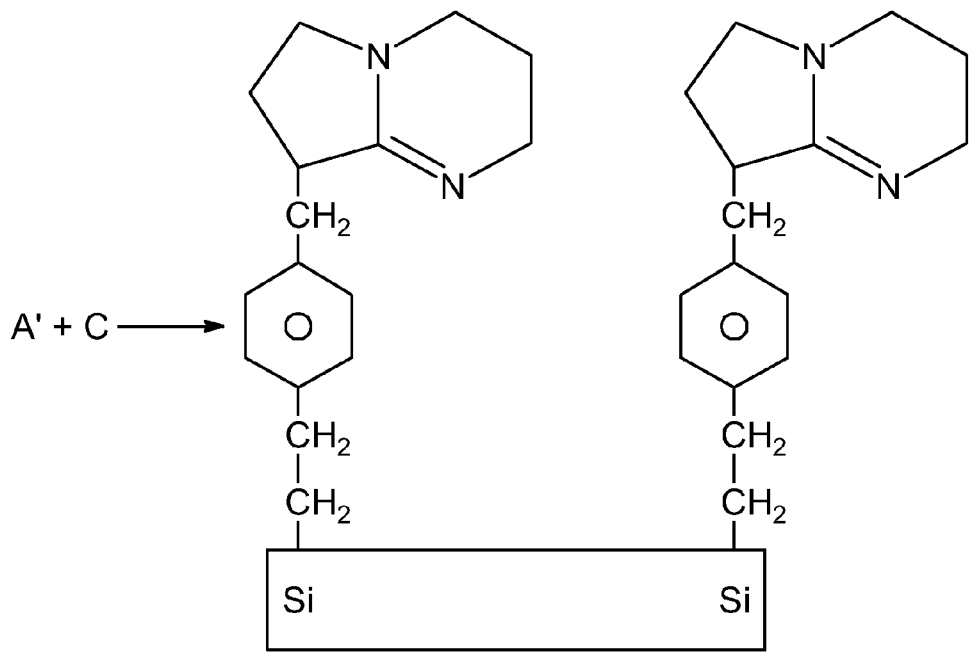
FIG. 13 illustrates the suspended silicon beam of FIG. 11 after reaction with deprotonated DBN to synthesize a functionalized surface connected by styrene moiety.

A similar approach may be followed for the DBN functionalization process. FIG. 13 shows an example final functionalized DBN based sensing surface.

In some embodiments, the functionalized reference surface 18 on the second beam 16 may be made right along with the DBU or DBN based functionalized sensing surface 14 on the first beam 12. The functionalized reference surface 18 may be made insensitive to carbon dioxide by reaction of the functionalized DBN (or DBU) based surface with HCl in order to inactivate the DBN (or DBU) moiety (e.g., by selective direct printing of liquid HCl on the site of the future second beam 16).

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

The invention claimed is:

1. A carbon dioxide sensor comprising:
a first beam that includes a functionalized surface, wherein the functionalized surface of the first beam is a silicon surface that is connected to a 1,8 DIAZA BICYCLO [5,4,0]UNDEC-7-ENE (DBU) by alkyl chains;
a second beam that includes a functionalized surface, wherein the functionalized surface of the second beam is a silicon surface that is connected to a 1,8 DIAZA BICYCLO [5,4,0]UNDEC-7-ENE (DBU) by alkyl chains, and wherein the functionalized surface of the second beam is altered to inhibit adsorption of carbon dioxide such that differential sensing of carbon dioxide may be performed by monitoring changes in the resonant frequency of the first beam relative to the resonant frequency of second beam;
a first frequency measuring circuit that measures the resonant frequency of the first beam; and
a second frequency measuring circuit that measures the resonant frequency of the second beam; and
a control that analyzes the signals from the first frequency measuring circuit and the second frequency measuring circuit to perform differential sensing for determining the amount of carbon dioxide exposure of the carbon dioxide sensor.

2. The carbon dioxide sensor of claim 1, wherein the functionalized surface of the second beam has been reacted with HCl to prevent changes to the resonant frequency of the second beam when the second beam is exposed to carbon dioxide.

3. The carbon dioxide sensor of claim 1 further comprising a substrate such that the first and second beams are formed on the substrate.

4. The carbon dioxide sensor of claim 1 wherein the functionalized surface of the first beam is part of the first beam and the functionalized surface of the second beam is part of the second beam.

5. The carbon dioxide sensor of claim 1 wherein the functionalized surface of the first beam is formed as part of a layer that is added to the first beam and the functionalized surface of the second beam is formed as part of a layer that is added to the second beam.

6. A carbon dioxide sensor comprising:
a first beam that includes a functionalized surface;
a second beam that includes a functionalized surface such that differential sensing of carbon dioxide may be performed by monitoring changes in the resonant frequency of the first beam relative to the resonant frequency of second beam, wherein the functionalized surface of the second beam has been reacted with HCl to prevent changes to the resonant frequency of the second beam when the second beam is exposed to carbon dioxide;
a first frequency measuring circuit that measures the resonant frequency of the first beam;
a second frequency measuring circuit that measures the resonant frequency of the second beam; and
a control that analyzes the signals from the first frequency measuring circuit and the second frequency measuring circuit to perform differential sensing for determining the amount of carbon dioxide exposure of the carbon dioxide sensor.

7. The carbon dioxide sensor of claim 6 further comprising a substrate such that the first and second beams are formed on the substrate.

8. The carbon dioxide sensor of claim 6 wherein the functionalized surface of the first beam is part of the first beam and the functionalized surface of the second beam is part of the second beam.

9. The carbon dioxide sensor of claim 6 wherein the functionalized surface of the first beam is formed as part of a layer that is added to the first beam and the functionalized surface of the second beam is formed as part of a layer that is added to the second beam.

10. A carbon dioxide sensor comprising:
a first beam that includes a functionalized surface, wherein the functionalized surface of the first beam is a silicon surface that is connected to a DIAZA-BICYCLO[4,3,0]-NON-5-ENE (DBN) by alkyl chains;
a second beam that includes a functionalized surface, wherein the functionalized surface of the second beam is a silicon surface that is connected to a 1,8 DIAZA BICYCLO [5,4,0]UNDEC-7-ENE (DBU) by alkyl chains, and wherein the functionalized surface of the second beam is altered to inhibit adsorption of carbon dioxide such that differential sensing of carbon dioxide may be performed by monitoring changes in the resonant frequency of the first beam relative to the resonant frequency of second beam;
a first frequency measuring circuit that measures the resonant frequency of the first beam; and
a second frequency measuring circuit that measures the resonant frequency of the second beam; and
a control that analyzes the signals from the first frequency measuring circuit and the second frequency measuring circuit to perform differential sensing for determining the amount of carbon dioxide exposure of the carbon dioxide sensor.

11. The carbon dioxide sensor of claim 10, wherein the functionalized surface of the second beam has been reacted with HCl to prevent changes to the resonant frequency of the second beam when the second beam is exposed to carbon dioxide.

12. A carbon dioxide sensor comprising:
a first beam that includes a functionalized surface, wherein the functionalized surface of the first beam is a silicon surface that is connected to a 1,8 DIAZA BICYCLO [5,4,0]UNDEC-7-ENE (DBU) by styrene moiety;
a second beam that includes a functionalized surface, wherein the functionalized surface of the second beam is a silicon surface that is connected to a 1,8 DIAZA BICYCLO [5,4,0]UNDEC-7-ENE (DBU) by styrene moiety, and wherein the functionalized surface of the second beam is altered to inhibit adsorption of carbon dioxide such that differential sensing of carbon dioxide may be performed by monitoring changes in the resonant frequency of the first beam relative to the resonant frequency of second beam;
a first frequency measuring circuit that measures the resonant frequency of the first beam; and
a second frequency measuring circuit that measures the resonant frequency of the second beam; and
a control that analyzes the signals from the first frequency measuring circuit and the second frequency measuring circuit to perform differential sensing for determining the amount of carbon dioxide exposure of the carbon dioxide sensor.

13. The carbon dioxide sensor of claim 12, wherein the functionalized surface of the second beam has been reacted with HCl to prevent changes to the resonant frequency of the second beam when the second beam is exposed to carbon dioxide.

14. A carbon dioxide sensor comprising:
a first beam that includes a functionalized surface, wherein the functionalized surface of the first beam is a silicon surface that is connected to a DIAZA-BICYCLO[4,3,0]-NON-5-ENE (DBN) by styrene moiety;
a second beam that includes a functionalized surface, wherein the functionalized surface of the second beam is a silicon surface that is connected to a DIAZA-BICYCLO[4,3,0]-NON-5-ENE (DBN) by styrene moiety, and wherein the functionalized surface of the second beam is altered to inhibit adsorption of carbon dioxide such that differential sensing of carbon dioxide may be performed by monitoring changes in the resonant frequency of the first beam relative to the resonant frequency of second beam;
a first frequency measuring circuit that measures the resonant frequency of the first beam; and
a second frequency measuring circuit that measures the resonant frequency of the second beam; and
a control that analyzes the signals from the first frequency measuring circuit and the second frequency measuring circuit to perform differential sensing for determining the amount of carbon dioxide exposure of the carbon dioxide sensor.

15. The carbon dioxide resonant sensor of claim 14, wherein the functionalized surface of the second beam has been reacted with HCl to prevent changes to the resonant frequency of the second beam when the second beam is exposed to carbon dioxide.

* * * * *